United States Patent [19]

Ax et al.

[11] 4,238,474

[45] Dec. 9, 1980

[54] AGGLUTINATION OF LYMPHOCYTES FOR DIAGNOSING MALIGNANT TUMOR

[75] Inventors: Wolfgang Ax; Hartwig W. Bauer; Sabine Schottler, all of Marburg, Fed. Rep. of Germany

[73] Assignee: Behringwerke Aktiengesellschaft, Marburg, Fed. Rep. of Germany

[21] Appl. No.: 890,913

[22] Filed: Mar. 28, 1978

[30] Foreign Application Priority Data

Mar. 29, 1977 [DE] Fed. Rep. of Germany ....... 2713742
Sep. 30, 1977 [DE] Fed. Rep. of Germany ....... 2744019

[51] Int. Cl.$^3$ ..................... G01N 33/48; G01N 33/50
[52] U.S. Cl. .................................... 424/12; 23/230 B; 424/2; 424/3; 424/8; 424/101
[58] Field of Search ................. 424/2, 3, 8, 12, 101; 23/230 B

[56] References Cited

PUBLICATIONS

Vanfurth, (Ed.), Mononuclear Phagocytes in Immunity, Infection & Path., Blackwell Sci. Pub., London, 1975, pp. 372-385.
Williams, Methods in Immunol. & Immunochem. Acd. Press, N.Y., vol. V, 1976, pp. 354-355.
Kabat, Experimental Immunochem. C. C. Thomas, Springfield, Ill., 2nd Ed., 1961, pp. 40-41.
Duksin, Chem. Abs., vol. 73, 1970, Ab. No. 118410u.
Carroll, Chem. Abs., vol. 76, 1972, Ab. No. 82391j.
Wagner, Chem. Abs., vol. 81, 1974, Ab. No. 105932f.
Siegel, Chem. Abs., vol. 83, 1975, Ab. No. 161995g.
Behnke, Chem. Abs., vol. 84, 1976, Ab. No. 13587f.
Marikovsky, Chem. Abs., vol. 84, 1976, Ab. No. 177515g.
Heier, Chem. Abs., vol. 86, 1977, Ab. No. 104220p.
Oliver, Chem. Abs., vol. 86, 1977, Ab. No. 14428h.
Vainer, Chem. Abs., vol. 81, 1974, Ab. No. 117920p.

*Primary Examiner*—Anna P. Fagelson
*Attorney, Agent, or Firm*—Curtis, Morris & Safford

[57] ABSTRACT

The invention provides a process for the specific agglutination of sensitized lymphocytes by adding to a dispersion of at least $10^5$ ml$^{-1}$ lymphocytes in a physiologically compatible medium at least 0.01 mg/ml of polylysine or at least 0.1 μg/ml of poly-ornithine and keeping the mixture at a temperature of from 20° to 40° C. for 20 minutes. The product is used for the diagnosis of malignant diseases.

3 Claims, No Drawings

AGGLUTINATION OF LYMPHOCYTES FOR DIAGNOSING MALIGNANT TUMOR

The invention relates to a process for the specific agglutination of lymphocytes of sensitized the peripheric blood, which is an important method in diagnostics for the detection of diseases accompanied by a changed agglutinability of the lymphocytes.

E. J. Field and E. A. Caspary observed a changed electrophoretic behavior of lymphocytes from patients suffering from cancer, upon addition of the encephalitogenic factor (cf. Lancet ii, page 1337, 1970).

According to D. Sabolovic et al., (cf. Br.J.Cancer, 1975, volume 32, pages 28 to 32), lymphocytes of patients suffering from malignant diseases have a different behavior than those of healthy donors, upon addition of histone F2Al.

However, both the encephalitogenic factor and histone fractions are not well defined compounds. Rather, their properties are influenced by the process for their preparation.

With regard to the importance of the identification of changed lymphocytes in comparison with standard types, the invention was confronted with the problem of developing a process for the agglutination of sensitized lymphocytes using defined chemical substances. The agglutinability of the blood lymphocytes shall be an index to the presence of malignant diseases or serve as a measure for identifying these diseases.

Sabolovic et al. (1975) have made trials to replace histone by poly-L-arginine or poly-L-lysine. However, poly-L-lysine proved to be unsuitable for agglutinating lymphocytes under the conditions chosen by Sabolovic.

It has now been found, surprisingly, not only that the use of poly-lysine or poly-ornithine makes an agglutination of lymphocytes of the peripheral blood possible, but furthermore that this agglutination permits a diagnostic identification concerning the presence of malignant diseases.

The subject of the present invention, consequently, is a process for the selective agglutination of sensitized lymphocytes, which comprises adding to a dispersion of $10^5$ ml$^{-1}$ lymphocytes in a physiologically compatible aqueous medium at least 0.01 mg/ml of poly-lysine or 0.1 μg/ml of polyornithine and keeping the mixture for at least 20 minutes at a temperature of from 20° to 40° C., advantageously in an atmosphere saturated with moisture.

An agglutination occurring during an incubation period of from 20 to 120 minutes can be considered as diagnostic index to the presence of malignant diseases.

A preferred poly-lysine for the process of the invention is that of molecular weight 1,000 to 100,000, especially of molecular weight 1,000 to 4,000. Poly-L-lysine, which may be obtained in substantially stable form as a salt, for example hydrobromide or hydrochloride, is used particularly preferably. Among poly-ornithines, preference is given to poly-L-ornithine, especially to that of molecular weight 40,000 to 60,000, preferably 53,000.

The lymphocytes are isolated from peripheral blood according to known methods. An isolation of the lymphocytes via a gradient is recommended, as the suspension of lymphocytes to be used should be free from further blood constituents as far as possible.

The blood obtained from the test person is rendered non-coagulating in usual manner, for example by adding an anticoagulant such as heparin, and subsequently the lymphocytes are recovered therefrom by known methods, for example by introducing the blood sample into a column charged with glass beads. Adherent cells adhere to the beads.

The lymphocytes can be recovered from the eluate by gradient centrifugation. Alternatively, an absorption of adherent cells on glass beads may be dispensed with so that gradient centrifugation can be directly employed in this case.

Further suitable processes for obtaining lymphocytes are described, by way of example, in the following references: Johnson G. J. and P. S. Russel, Nature 208, page 343, (1965); A. Boyum, Scand.J.Clin.Lab.Invest-.Suppl. 77, (1966); J. J. Oppenheimer, B. G. Leventhal, E. M. Hersh, Journal Immunolog. 101, pages 262-270, (1968); J. J. Twomey, O. Sharkey, Journal Immunolog. 108, pages 984-990, (1972).

All of the lymphocytes, which have been obtained and purified by one of the above methods, may be brought to agglutination using poly-L-lysine or poly-ornithine under the conditions of the above process.

The use of a so-called test plate is recommended for carrying out the agglutination of the lymphocytes in a diagnostic laboratory. This test plate is generally made of a plastic which is provided with one or several series of depressions. When adding poly-lysine to suspensions of lymphocytes which have been poured into the depressions, the agglutination may be microscopically observed.

The use of test plates made of optionally flawless plastic, for example of transparent polystyrene, is recommended to insure a better microscopic reading. The bottom of each depression is shaped as a flat plate. The test plates are generally intended for single use. Test plates of this type are provided with about 60 depressions over an area of about 60×80 mm.

A differentiated diagnosis may be made by adding poly-lysine or poly-L-ornithine to suspensions of lymphocytes in varying concentrations, because agglutination occurs either earlier or later depending on the concentrations employed and on the diseases present. For example, when 0.01 to 0.1 mg/ml (preferably 0.05 mg/ml) of a poly-lysine (preferably a poly-L-lysine) having a molecular weight of 1000 to 4000 (3400 on the average) is added to $5 \times 10^5$ to $5 \times 10^7$ lymphocytes, and when the mixture is kept for 30 to 60 minutes at a temperature of from 30° to 40° C., only lymphocytes from patients suffering from malignant diseases, for example bronchial tumor, carcinoma of the colon, carcinoma of the rectum, tumor of the thyroid, carcinoma of the stomach, carcinoma of the breast, carcinoma of the pancreas, malignant lymphoma, and from patients suffering from comparable malignant diseases, agglutinate. The same applies to the case in which 0.001 to 0.1 mg/ml (preferably 0.01 mg/ml) of poly-ornithine (preferably poly-L-ornithine) having a molecular weight of 40000 to 60000 (53000 on the average) is added to $5 \times 10^5$ to $5 \times 10^7$ lymphocytes and the mixture is kept at a temperature of from 30° to 40° C. for a period of from 30 to 60 minutes.

Agglutinations which occur beyond the indicated periods of time and conditions are not considered as being caused by malignant diseases. However, it is quite natural that the diagnostic indication cannot guarantee 100 percent certainty. In this method, too, like in any other diagnostic method, false-negative and false-positive results may be obtained; but they are generally within a range of from 2 to 3%.

The process for the agglutination of lymphocytes may be carried out in especially simple manner by first placing poly-lysine or poly-ornithine into the test receptacle and adding thereto an aqueous suspension of the lymphocytes. For this purpose, a so-called test system may be suitably employed which is composed of the above-described test plate made of a plastic. Poly-lysine is present in each of the depressions of this plate in an amount of from 0.1 to 1 μg or poly-ornithine in an amount of from 0.001 to 1 μg.

For obtaining test systems of this kind, a solution of poly-lysine or poly-ornithine in distilled water is poured into each of the depressions so that the above-indicated quantity of poly-lysine or poly-ornithine is retained on drying. The agglutination process may be performed as described above by adding the dispersion of lymphocytes.

Consequently, a further subject of the present invention is a test plate made of a plastic which is provided with depressions, each depression containing, in dried form, 0.1 to 1 μg of a poly-lysine of molecular weight 1,000 to 4,000, on the average 3,400, or 0.001 to 1 μg of a poly-L-ornithine of molecular weight 40,000 to 60,000, on the average 53,000. Like poly-lysine or poly-ornithine even test plates of said kind containing these substances are similarly advantageously kept at temperatures below 0° C., with the exclusion of humidity.

The invention is illustrated in the following examples, which demonstrate the preparation of suitable lymphocytes and the mode of carrying out the agglutination process.

EXAMPLE 1

6 ml of venous blood to which heparin has been added is diluted with Hank's solution in a ratio of 1:2 and is thereafter applied onto a two-layer gradient which consists of two 5 ml layers of solutions having different densities.

The layer A (top layer) consists of sodium, potassium, magnesium and methylglucamine salts of metrizoic acid RONPACON (registered trade mark of the firm Cilag-Chemie GmbH, Alsbach, Germany) and a high-molecular weight copolymer of saccharose and epichlorohydrine FICOLL (registered trade mark of the firm Pharmacia, Uppsala, Sweden) of density 1.077.

The layer B (bottom layer) consists of the above substances, but has the density 1.119.

The diluted blood, applied onto the gradient, is centrifuged at 800 g for 20 minutes. The ring of lymphocytes lying over A is siphoned off, washed three times with Hank's solution and the number of the lymphocytes is adjusted to $6 \times 10^6$/ml.

Poly-L-lysine (molecular weight 3,400; of the firm Sigma, Munich, Germany) is dissolved in 0.145 mol/l of NaCl, of pH 7.0 (0.05 mg/ml). 10 μl of this solution are incubated in microtest plates (of the firm Greiner, Nürtingen, Germany) with the same volume of the suspension of lymphocytes, for 30 minutes, at 37° C., in a humid atmosphere, and are thereafter evaluated microscopically.

EXAMPLE 2

A suspension of lymphocytes is prepared in the manner described in Example 1.

Poly-L-ornithine (molecular weight 53,000; of the firm Sigma, Munich, Germany) is dissolved in 0.145 mol/l of NaCl, of pH 7.0 (0.01 mg/ml). 10 μg of this solution is incubated in microtest plates (of the firm Greiner, Nürtingen, Germany) with the same volume of the suspension of lymphocytes, in a humid atmosphere, for 30 minutes, at 37° C. and are thereafter evaluated microscopically.

What is claimed is:

1. A method for diagnosing a malignant tumor in a patient possibly suffering therefrom, which method comprises subjecting the patient's lymphocytes to a specific agglutination by adding at least 0.01 mg/ml of polylysine having a molecular weight between 1000 and 4000, or at least 0.1 g/ml of polyornithine having a molecular weight between 40000 and 60000, to a dispersion of at least $10^5$/ml of intact lymphocytes in a physiologically compatible aqueous medium and keeping the mixture at a temperature from 20° C. to 40° C. for at least 20 minutes.

2. The method as in claim 1 wherein 0.05 mg/ml of polylysine is added to between $5 \times 10^5$/ml and $5 \times 10^7$/ml of lymphocytes and the mixture is kept at a temperature from 30° C. to 40° C. for 30 to 60 minutes.

3. The method as in claim 1 wherein from 0.001 mg/ml to 1 mg/ml of poly-L-ornithine is added to between $5 \times 10^5$/ml and $5 \times 10^7$/ml of lymphocytes and the mixture is kept at a temperature from 30° C. to 40° C. for 30 to 60 minutes.

* * * * *